(12) United States Patent
Kawamura

(10) Patent No.: US 6,632,543 B1
(45) Date of Patent: Oct. 14, 2003

(54) AMINE COMPOUND AND ORGANIC ELECTROLUMINESCENCE DEVICE USING THE COMPOUND

(75) Inventor: Hisayuki Kawamura, Chiba (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 39 days.

(21) Appl. No.: 09/831,883

(22) PCT Filed: Sep. 27, 2000

(86) PCT No.: PCT/JP00/06656

§ 371 (c)(1),
(2), (4) Date: May 22, 2001

(87) PCT Pub. No.: WO01/23344

PCT Pub. Date: May 4, 2001

(30) Foreign Application Priority Data

Sep. 30, 1999 (JP) ............................................ 11-277954

(51) Int. Cl.[7] .............................. B32B 19/00; B32B 9/00
(52) U.S. Cl. ........................ 428/690; 428/913; 313/504; 313/506; 564/305; 564/429
(58) Field of Search ................................ 428/690, 913; 313/504, 506; 564/305, 429

(56) References Cited

U.S. PATENT DOCUMENTS

| | | | | |
|---|---|---|---|---|
| 5,759,444 A | * | 6/1998 | Enokida et al. ............ | 252/301.6 |
| 5,811,834 A | * | 9/1998 | Tamano et al. ............. | 257/40 |
| 5,948,941 A | * | 9/1999 | Tamano et al. ............. | 564/315 |
| 6,074,734 A | * | 6/2000 | Kawamura et al. ......... | 428/220 |
| 6,280,859 B1 | * | 8/2001 | Onikubo et al. ............ | 428/690 |
| 6,344,283 B1 | * | 2/2002 | Inoue et al. ................. | 428/690 |

FOREIGN PATENT DOCUMENTS

| | | |
|---|---|---|
| EP | 0 699 654 | 3/1996 |
| EP | 0 891 121 | 1/1999 |

OTHER PUBLICATIONS

David Terrell, Research Disclosure, No. 339, pp. 571–573, "Electroluminescent Device and Substances Suited for Use Therein", Jul. 1992.

* cited by examiner

*Primary Examiner*—Cynthia H. Kelly
*Assistant Examiner*—Camine S Thompson
(74) *Attorney, Agent, or Firm*—Oblon, Spivak, McClelland, Maier & Neustadt, P.C.

(57) ABSTRACT

An amine compound having a m-terphenyl group exhibits excellent heat resistance when the compound is used as a material constituting an organic electroluminescence device (an organic EL device). An organic EL device using the amine compound exhibits excellent luminance of emitted light and a long life. An organic EL device which contains the amine compound and an aromatic compound having a specific styryl group is also disclosed.

13 Claims, No Drawings

AMINE COMPOUND AND ORGANIC ELECTROLUMINESCENCE DEVICE USING THE COMPOUND

TECHNICAL FIELD

The present invention relates to a novel amine compound and an organic electroluminescence device (electroluminescence will be referred to as EL, hereinafter) using the amine compound and, more particularly, to an amine compound useful as a material constituting an organic EL device and an organic EL device which uses the amine compound and has a long life.

BACKGROUND ART

Organic EL devices are studied widely since the organic EL devices are completely solid devices and light weight thin displays driven under a low voltage and planar light sources can be prepared by using such devices.

In the application to displays, the organic EL devices have a drawback in that luminance of light emission decreases in a short time.

To overcome the drawback, improvements in a hole transporting material have been attempted.

For example, as disclosed in U.S. Pat. No. 5,061,569, it is known that the half-life of emission can be improved by using an amine derivative having a condensed aromatic ring such as N,N'-di(naphthyl-1-yl)-N,N'-diphenyl-4,4'-benzidine (referred to as NPD, hereinafter) as the hole transporting material.

However, since the above material has a glass transition temperature (Tg) as low as 100° C., an organic EL device using this material has a drawback in that the organic EL device has a short life time when the organic EL device is stored or used at a high temperature. In other words, the organic EL device has insufficient heat resistance. As another example, it is disclosed in the specification of Japanese Patent Application Laid-Open No. Heisei 8(1996)-48656 that an aromatic diamine derivative having at least biphenyl group as a substituent is used as the hole transporting material.

However, the above material has a drawback in that purification of the material is not easy since biphenyl group is too rigid and solubility of the diamine derivative having biphenyl group in organic solvents is poor. As the result, a material containing a great amount of impurities is obtained in industrial production of the aromatic diamine derivative and an organic EL device using the diamine derivative has insufficient heat resistance.

Moreover, an organic EL device using the above amine derivative has insufficient properties other than the heat resistance such as insufficient luminance of light emission and life time of luminance.

DISCLOSURE OF THE INVENTION

The present invention has been made under the above circumstances and has an object of providing a novel amine compound which has excellent solubility in organic solvents and can be produced easily, an organic EL device using the amine compound which has excellent heat resistance and an organic EL device using the amine compound which exhibits an excellent luminance of light emission and has a long life of luminance.

As the result of extensive studies by the present inventors to achieve the above object, it was found that the object can be achieved by an amine compound having a specific structure. The present invention has been completed based on the knowledge.

The present invention provides:

(1) An amine compound represented by following general formula (I):

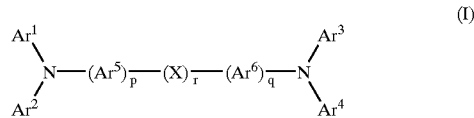

(In formula (I), $Ar^1$, $Ar^2$, $Ar^3$ and $Ar^4$ each represent an aryl group having 5 to 30 nuclear atoms which may have substituents, at least one of $Ar^1$, $Ar^2$, $Ar^3$ and $Ar^4$ represents a m-terphenyl group, $Ar^5$ and $Ar^6$ each represent an arylene group having 5 to 30 nuclear atoms which may have substituents, X represents O, S, an alkylene group having 1 to 6 carbon atoms, an arylene group having 5 to 30 nuclear atoms or diphenylmethylene group, p and q each represent an integer of 0 to 3, r represents a number of 0 or 1 and $p+q \geq 1$);

(2) An amine compound described in (1), wherein at least one of $Ar^1$, $Ar^2$, $Ar^3$ and $Ar^4$ represents a m-terphenyl group and the rest of $Ar^1$, $Ar^2$, $Ar^3$ and $Ar^4$ represent phenyl group or naphthyl group;

(3) An amine compound described in any of (1) and (2), wherein the m-terphenyl group is a group expressed by following formula (II):

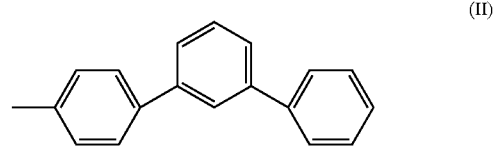

(4) An organic EL device comprising at least an organic light emitting layer disposed between a pair of electrodes, which device comprises an amine compound described in any of (1) to (3);

(5) An organic EL device described in (4), which comprises an amine compound described in any of (1) to (3) in a hole transporting area;

(6) An organic EL device described in (4), which comprises an amine compound described in any of (1) to (3) in a hole transporting layer; and (7) An organic EL device described in any of (4) to (6), which comprises in the organic light emitting area a compound selected from aromatic compounds having a styryl group which are represented by following general formulae (III) to (V):

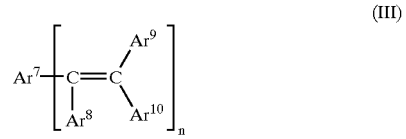

(In general formula (III), $Ar^7$ represents an aromatic group having 5 to 40 nuclear atoms which may have substituents, $Ar^8$, $Ar^9$ and $Ar^{10}$ each represent hydrogen atom or an aryl group having 5 to 30 nuclear atoms which may have substituents, at least one of $Ar^8$, $Ar^9$ and $Ar^{10}$ represents an aryl group which may have substituents and n represents an integer of 1 to 6)

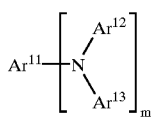

(In general formula (IV), $Ar^{11}$ represents an aromatic group having 5 to 30 nuclear atoms which may have substituents, $Ar^{12}$ and $Ar^{13}$ each represent hydrogen atom or an aryl group having 5 to 30 nuclear atoms which may have substituents, at least one of the groups represented by $Ar^{11}$, $Ar^{12}$ and $Ar^{13}$ is substituted with a styryl group which may have substituents and m represents an integer of 1 to 6), and

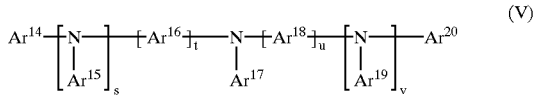

(In general formula (V), $Ar^{14}$ and $Ar^{20}$ each represent an aryl group having 5 to 30 nuclear atoms which may have substituents, $Ar^{15}$ to $Ar^{19}$ each represent hydrogen atom or an aromatic group having 5 to 30 nuclear atoms which may have substituents, at least one of the groups represented by $Ar^{15}$ to $Ar^{19}$ is substituted with a styryl group which may have substituents and s, t, u, and v each represent a number of 0 or 1).

THE MOST PREFERRED EMBODIMENT TO CARRY OUT THE INVENTION

The organic compound of the present invention is a compound represented by the general formula (I):

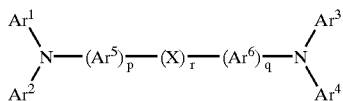

In the above general formula (I), $Ar^1$, $Ar^2$, $Ar^3$ and $Ar^4$ each represent an aryl group having 5 to 30 nuclear atoms which may have substituents and at least one of $Ar^1$, $Ar^2$, $Ar^3$ and $Ar^4$ represents a m-terphenyl group Examples of the aryl group having 5 to 30 nuclear atoms include phenyl group, biphenyl group, naphthyl group, anthranyl group, terphenyl group, phenanthryl group, pyrenyl group, chrysenyl group, pyrrolyl group, furanyl group, thiophenyl group, oxazolyl group, oxadiazolyl group, benzofuranyl group, carbazolyl group, isobenzolyl group, quinolyl group, pyrimidyl group and quinoxanyl group. Among these groups, phenyl group, naphthyl group, biphenyl group, anthranyl group, phenanthryl group and terphenyl group are preferable and phenyl group and naphthyl group are more preferable.

The above groups represented by $Ar^1$, $Ar^2$, $Ar^3$ and $Ar^4$ may be the same with or different from each other. It is necessary that at least one of the groups represented by $Ar^1$, $Ar^2$, $Ar^3$ and $Ar^4$ be a m-terphenyl group which may have substituents.

The m-terphenyl group present in the amine compound represented by general formula (I) of the present invention is a monovalent group obtained by removing one hydrogen atom from a m-terphenyl composed of three benzene rings which are not condensed and bonded to each other in a manner such that the central benzene ring is bonded to the other two benzene rings at the m-positions.

Therefore, the m-terphenyl group is represented by general formula (II'). Nitrogen atom may be bonded at various positions in the m-terphenyl group. Compounds represented by general formula (II') in which nitrogen atom is bonded at the 3-, 4-, 5-, 2'- or 5'-position are easily available. Among these compounds, the compound in which nitrogen atom is bonded at the 4-position, i.e., the m-terphenyl expressed by formula (II), is preferably used as the amine compound of the present invention since the compound can be prepared easily.

As described above, the m-terphenyl group may have substituents.

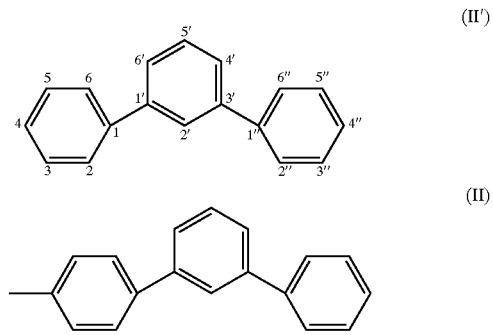

In general formula (I), $Ar^5$ and $Ar^6$ each represent an arylene group having 5 to 30 nuclear atoms which may have substituents. Examples of the arylene group having 5 to 30 nuclear atoms include phenylene group, biphenylene group, naphthylene group, anthranylene group, terphenylene group, phenanthrylene group, pyrenylene group, chrysenylene group, fluorenylene group, pyrrolylene group, furanylene group, thiophenylene group, oxazolylene group, oxadiazolylene group, benzofuranylene group, carbazolyene group and isobenzofuranylene group.

Examples of the substituent which the group represented by $Ar^1$ to $Ar^6$ may have include alkyl groups having 1 to 6 carbon atoms, aryl groups having 5 to 30 nuclear atoms, styryl groups having 8 to 30 carbon atoms, alkoxy groups having 1 to 6 carbon atoms, aryloxy groups having 5 to 18 carbon atoms, aralkyloxy groups having 7 to 18 carbon atoms, amino groups substituted with aryl groups having 5 to 16 carbon atoms, nitro group, cyano group, ester groups having 1 to 6 carbon atoms and halogen atoms.

Examples of the alkyl group having 1 to 6 carbon atoms include methyl group, ethyl group, propyl group, isopropyl group, n-butyl group, sec-butyl group, tert-butyl group, n-pentyl group, n-hexyl group, cyclopentyl group and cyclohexyl group. Examples of the aryl group having 5 to 30 nuclear atoms include the groups described as the examples of the groups represented by $Ar^1$ to $Ar^4$.

Examples of the styryl group having 8 to 30 carbon atoms include 1-phenylvinyl-1-yl group, 2-phenylvinyl-1-yl group, 2,2-diphenylvinyl-1-yl group, 2-phenyl-2-(naphthyl-1-yl)vinyl-1-yl group and 2,2-bis(diphenyl-1-yl)vinyl-1-yl group. Among these groups, 2,2-diphenylvinyl-1-yl group is preferable.

Examples of the alkoxy group having 1 to 6 carbon atoms include methoxy group, ethoxy group, propoxy group, isopropoxy group, n-butoxy group, sec-butoxy group, tert-butoxy group, n-pentyloxy group, n-hexyloxy group, cyclopentyloxy group and cyclohexyloxy group.

Examples of the aryloxy group having 5 to 18 carbon atoms include phenoxy group, biphenyloxy group, tolyloxy group, naphthyloxy group, anthranyloxy group, phenanthryloxy group, terphenyloxy group, pyrenyloxy group, chrysenyloxy group, pyrrolyloxy group, furanyloxy group, thiophenyloxy group, oxyazolyloxy group, oxadiazolyloxy group, benzofuranyloxy group, carbazolyloxy group, isobenzofuranyloxy group, quinolyloxy group, pyrimidyloxy group and quinoxalyloxy group.

Examples of the aralkyloxy group having 7 to 18 carbon atoms include benzyloxy group, phenetyloxy group and naphthylmethoxy group. Examples of the amino group substituted with aryl groups having 5 to 16 carbon atoms include diphenylamino group, dinaphthylamino group, naphthylphenylamino group and ditolylamino group. Examples of the ester group having 1 to 6 carbon atoms include methoxycarbonyl group, ethoxycarbonyl group, propoxycarbonyl group and isopropoxycarbonyl group. Examples of the halogen atom include fluorine atom, chlorine atom and bromine atom.

The above substituents may form a ring, which may be bonded to the above group. When two or more substituents are bonded at adjacent positions, the substituents may be bonded to each other and form a ring structure.

In the above general formula (I), X represents O, S, an alkylene group having 1 to 6 carbon atoms such as methylene group, ethylene group, n-propylene group, isopropylene group and cyclopropylene group, an arylene group having 5 to 30 nuclear atoms or diphenylmethylene group. The diphenylmethylene group may be substituted with alkyl groups or alkoxy groups each having 1 to 6 carbon atoms. Examples of the alkyl group and the alkoxy group include the groups described above as the examples of the substituents which the groups represented by $Ar^1$ to $Ar^6$ may have. r represents a number of 0 or 1. Examples of the arylene group include the groups described above as the examples of the groups represented by $Ar^5$ and $Ar^6$.

In the above general formula (1), p and q represent an integer of 0 to 3 and $p+q \geq 1$.

Specific examples of the amine compound represented by general formula (I) are shown in the following:

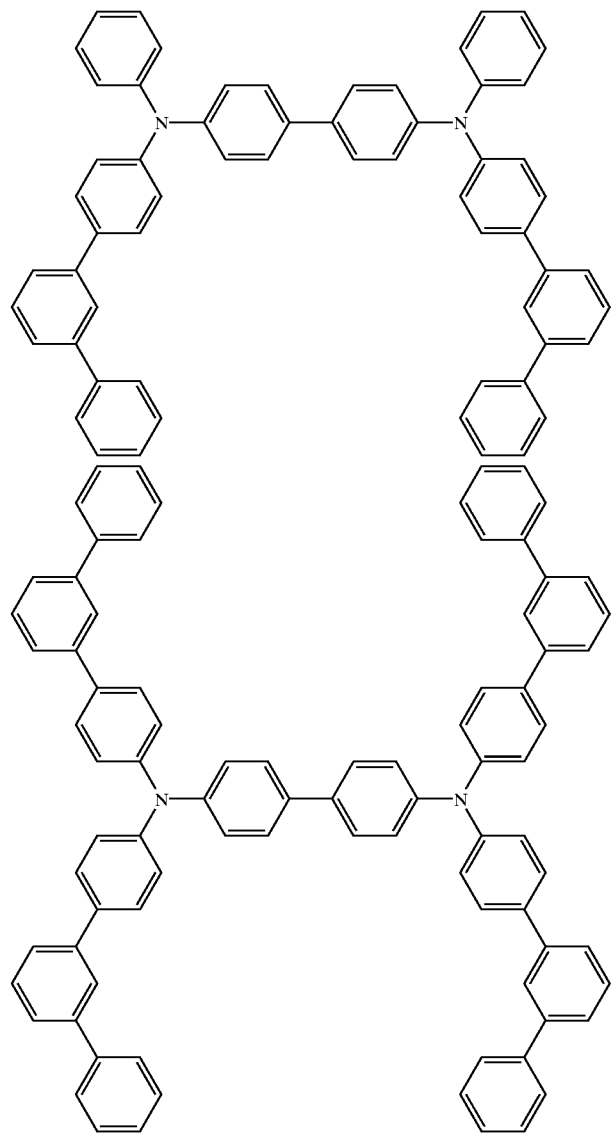

-continued
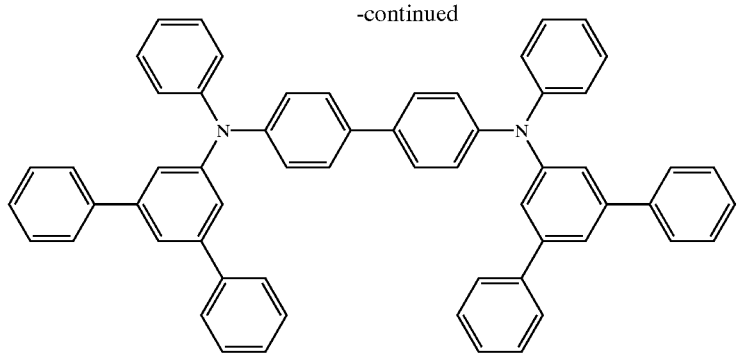
MT-03
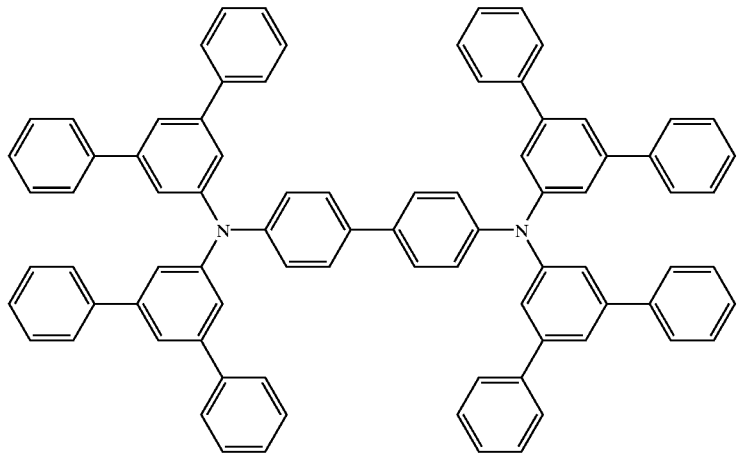
MT-04
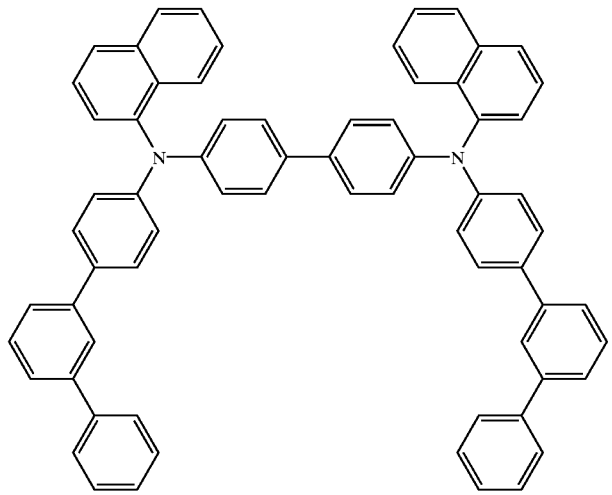
MT-05
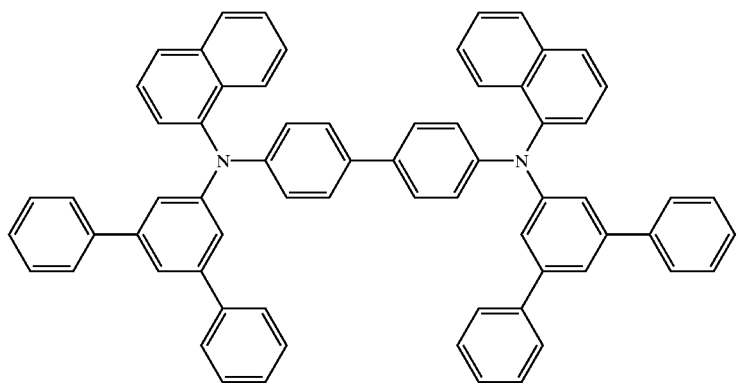
MT-06

MT-07
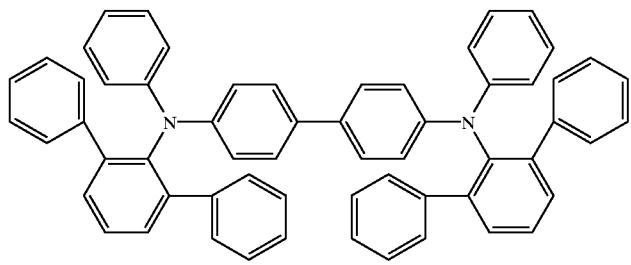
MT-08
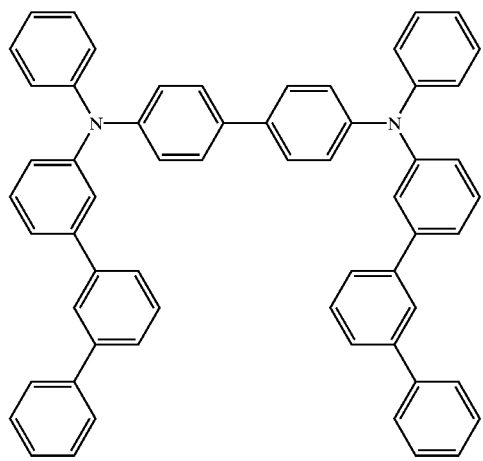
MT-09
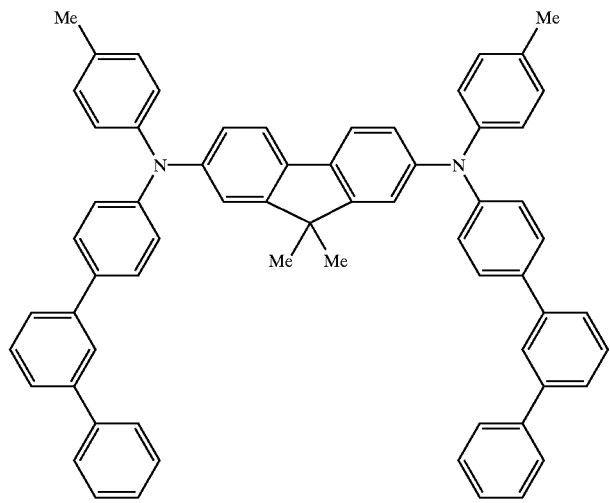

MT-10
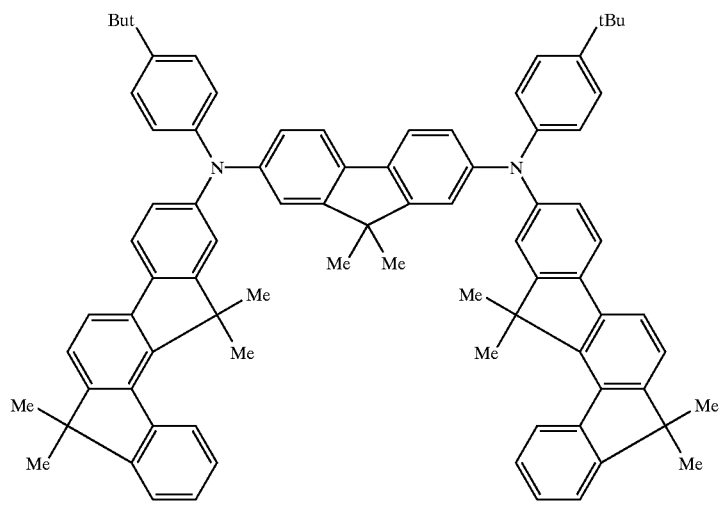
MT-11
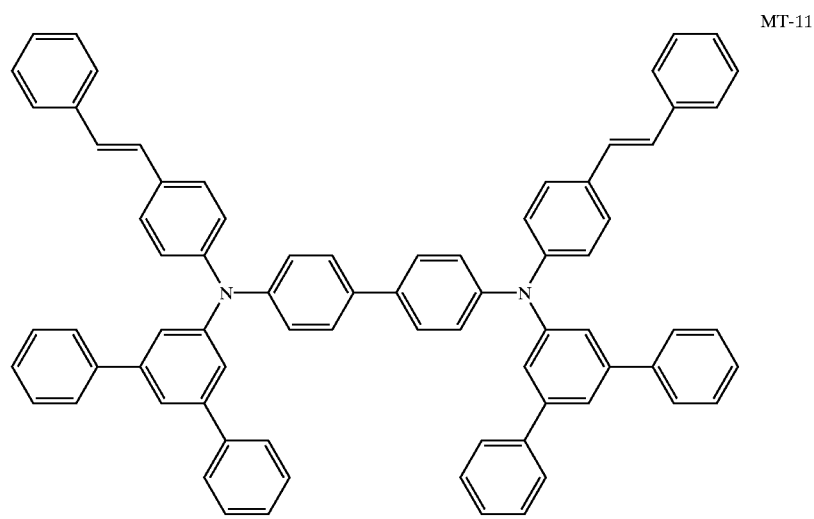
MT-12
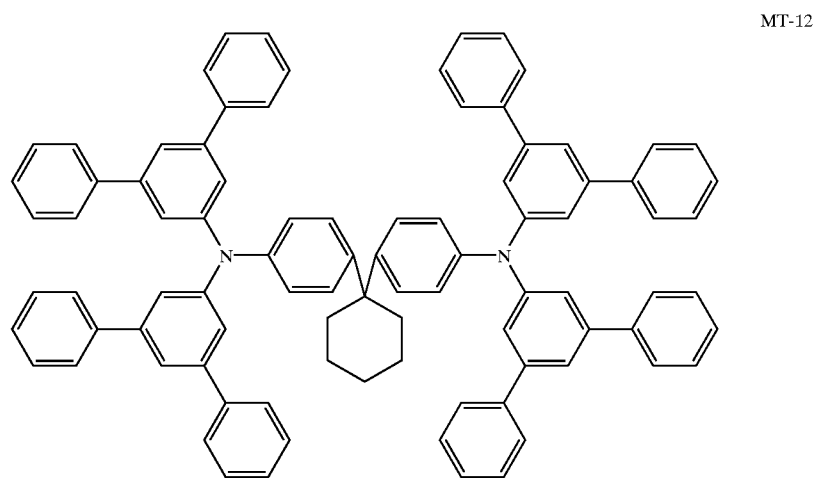

-continued
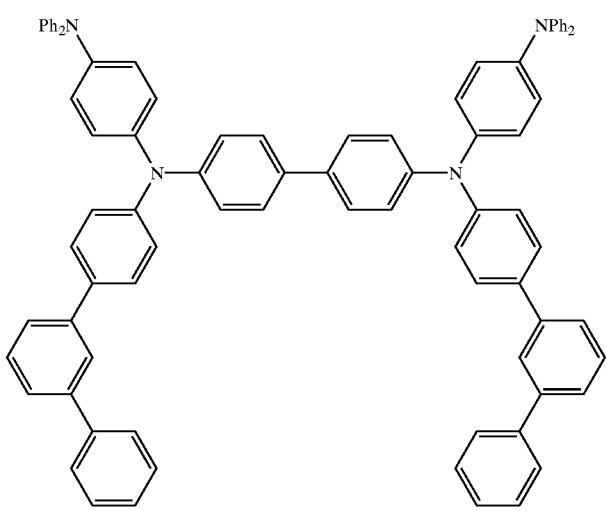
MT-13
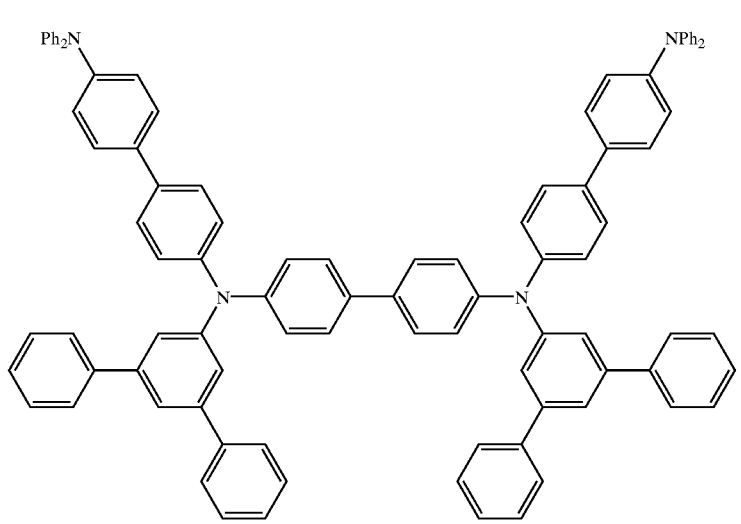
MT-14
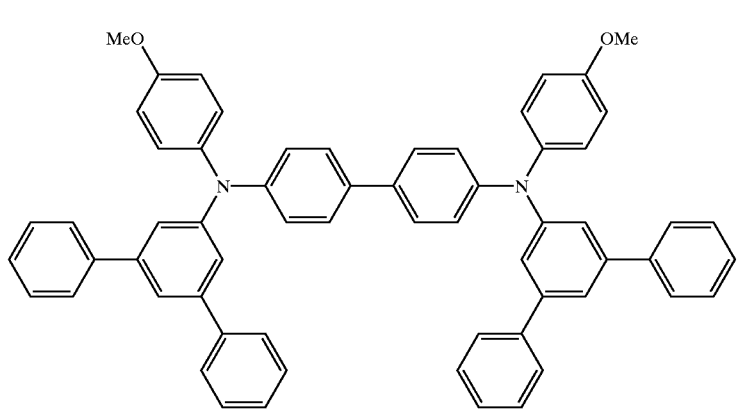
MT-15

-continued

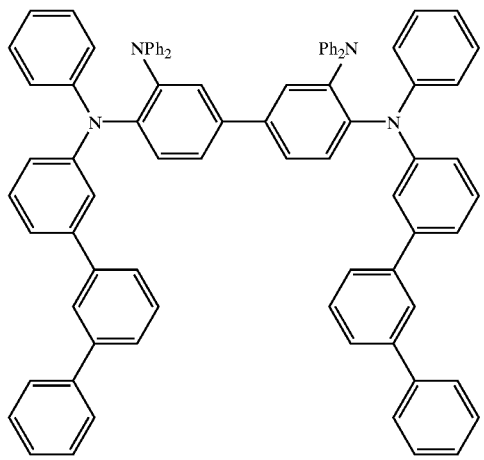

MT-16

The process for producing the amine compound represented by general formula (I) of the present invention is not particularly limited and various processes can be used. For example, a desired amine compound can be prepared by a combination of the Ullmann reaction and the Grignard reaction.

The organic EL device of the present invention is a device which comprises at least an organic light emitting layer disposed between a pair of electrodes. A device comprising the above amine compound in a light emitting area and, in particular, in a hole transporting layer is preferable.

Typical constructions of the organic EL device are as follows:

(1) An anode/a light emitting layer/a cathode
(2) An anode/a hole injecting layer/a light emitting layer/a cathode
(3) An anode/a light emitting layer/an electron injecting layer/a cathode
(4) An anode/a hole injecting layer/a light emitting layer/ an electron injecting layer/a cathode
(5) An anode/a layer of an organic semiconductor/a light emitting layer/a cathode
(6) An anode/a layer of an organic semiconductor/an electron barrier layer/a light emitting layer/a cathode
(7) An anode/a layer of an organic semiconductor/a light emitting layer/a layer for improvement of adhesion/a cathode
(8) An anode/a hole injecting layer/a hole transporting layer/a light emitting layer/an electron injecting layer/a cathode
(9) An anode/an insulating layer/a light emitting layer/an insulating layer/a cathode
(10) An anode/a layer of an inorganic semiconductor/an insulating layer/a light emitting layer/an insulating layer/a cathode
(11) An anode/a layer of an organic semiconductor/an insulating layer/a light emitting layer/an insulating layer/a cathode
(12) An anode/an insulating layer/a hole injecting layer/a hole transporting layer/a light emitting layer/an insulating layer/a cathode
(13) An anode/an insulating layer/a hole injecting layer/a hole transporting layer/a light emitting layer/an electron injecting layer/a cathode However, the construction of the organic EL device is not limited to the above constructions.

Among these constructions, in general, the construction shown in (8) is preferably used. It is preferable that the amine compound represented by general formula (I) is comprised in the hole transporting area among the above elements constituting the device.

The hole transporting area is an area in which holes move and, specifically, the hole injecting layer and the transporting layer.

It is preferable that the content of the above amine compound in the hole transporting area is 30 to 100% by mole of the total molecules in the hole transporting area.

The organic EL device is, in general, prepared on a substrate transmitting light. The substrate transmitting light is a substrate which supports the organic EL device and preferably a smooth and flat plate having a transmittance of light in the visible range of 400 to 700 nm of 50% or greater.

As the substrate transmitting light, for example, a glass plate or a plate of a polymer is used. Examples of the glass plate include plates of soda lime glass, glass containing barium and strontium, lead glass, aluminosilicate glass, borosilicate glass, barium borosilicate glass and quartz. Examples of the plate of a polymer include plates of polycarbonates, acrylic polymers, polyethylene terephthalate, polyether sulfides and polysulfones.

As the anode, an electrode made of an electrode material such as a metal, an alloy, an electrically conductive compound and a mixture of these materials, which has a great work function (4 eV or greater), is preferably used. Specific examples of the electrode material include metals such as Au and electrically conductive materials such as CuIn, ITO, $SnO_2$ and ZnO.

The anode can be prepared by forming a thin film of the above electrode material in accordance with the vapor deposition process or the sputtering process.

When light emitted from the light emitting layer is obtained through the anode, it is preferable that the transmittance of the emitted light through the anode is greater than 10%. It is also preferable that the sheet resistivity of the anode is several hundred Ω/□ or smaller. The thickness of the anode is selected, in general, in the range of 10 nm to 1 μm and preferably in the range of 10 to 200 nm.

As the light emitting layer in the organic EL of the present invention, a layer having the combination of the following functions is preferably used.

(1) The injecting function: the function of injecting holes from the anode or the hole injecting layer or injecting electrons from the cathode or the electron injecting layer when an electric field is applied.

(2) The transporting function: the function of transporting injected charges (electrons and holes) by the force of the electric field.

(3) The light emitting function: the function of providing the field for recombination of electrons and holes and emitting light generated by the recombination.

The easiness of injection of holes may be different from the easiness of injection of electrons. The ability of transporting holes expressed by the mobility of holes may be different from the ability of transporting electrons expressed by the mobility of electrons. It is preferable that either holes or electrons are transported.

The light emitting material in the organic EL device mainly comprises organic compounds. Specifically, compounds shown in the following are used in accordance with the desired color tone. For example, to obtain light emission in the region of ultraviolet region to purple, a compound represented by the following general formula (VI) is preferably used:

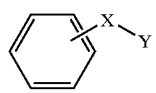 (VI)

wherein X represents a group represented by the following general formula:

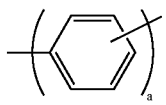

$a$ representing a number of 2, 3, 4, or 5, and Y represents the following group:

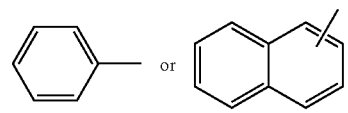

In the compound represented by general formula (VI), phenyl group, phenylene group and naphthyl group may have a single or a plurality of substituents selected from alkyl groups and alkoxy groups each having 1 to 4 carbon atoms, hydroxyl group, sulfonyl group, carbonyl group, amino group, dimethylamino group and diphenylamino group. These groups may be bonded to each other and form a saturated five-membered or six-membered group. In the compound, it is preferable that the bond is formed at the para-position of phenyl group, phenylene group and naphthyl group since the bonding is rigid and a smooth film is formed by vapor deposition without chemical decomposition. Specific examples of the compound represented by general formula (VI) include the following compounds:

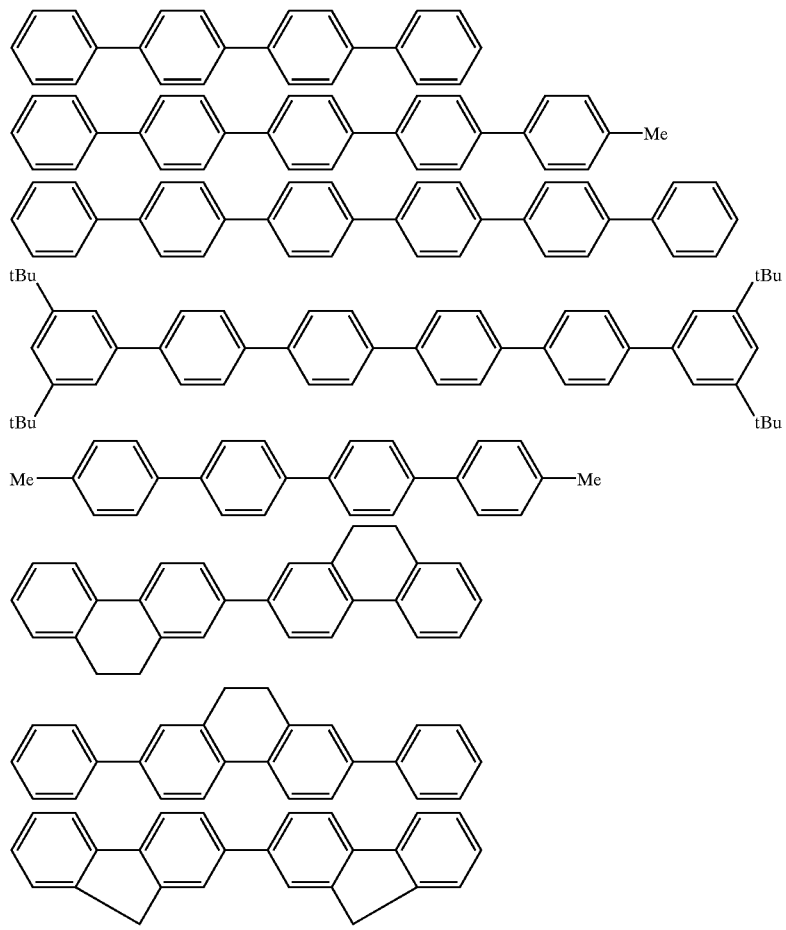

-continued

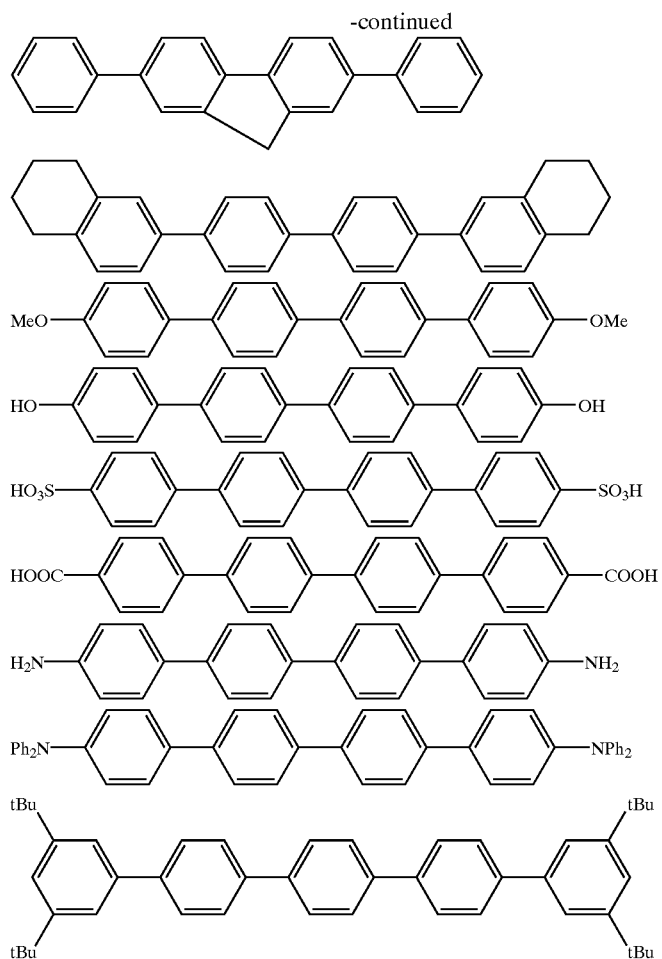

Among the compounds shown in the above, p-quarterphenyl derivatives and p-quinquephenyl derivatives are preferable.

To obtain emission of blue to green light, for example, a fluorescent whitening agent of benzothiazole, benzimidazole or benzoxazole, a metal chelate compound of an oxinoid compound or a styrylbenzene compound can be used.

Examples of the above compounds include compounds disclosed in Japanese Patent Application Laid-Open No. Showa 59(1984)-194393. Further examples of the compound useful as the above compound include compounds listed in Chemistry of Synthetic Dies, 1971, pages 628 to 637 and 640.

As the metal chelate compound of an oxinoid compound, for example, compounds disclosed in Japanese Patent Application Laid-Open No. Showa 63(1988)-295695 can be used. Typical examples of the above compound include metal complexes of 8-hydroxyquinolines such as tris(8-quinolinol) aluminum (referred to as Alq, hereinafter) and dilithiumepintridione.

As the styrylbenzene compound, for example, compounds disclosed in European Patent Nos. 0319881 and 0373582 can be used. Distyrylpirazine derivatives disclosed in Japanese Patent Application Laid-Open No. Heisei 2(1990)-252793 can also be used as the material of the light emitting layer. Polyphenyl compounds disclosed in European Patent No. 0387715 can also be used as the material of the light emitting layer.

Compounds other than the fluorescent whitening agents, metal chelate compounds of oxinoid compounds and styrylbenzene compounds can be used as the material of the light emitting layer. Examples of such compounds include the following compounds: 12-phthaloperinone (J. Appl. Phys., Volume 27, L713 (1988)); 1,4-diphenyl-1,3-butadiene and 1,1,4,4-tetraphenyl-1,3-butadiene (Appl. Phys, Lett., Volume 56, L799 (1990)); naphthalimide derivatives (Japanese Patent Application Laid-Open No. Heisei 2(1990)-305886); perylene derivatives (Japanese Patent Application Laid-Open No. Heisei 2 (1990)-189890); oxadiazole derivatives (Japanese Patent Application Laid-Open No. Heisei 2 (1990)-216791 and HAMADA et al., the 38th Associated Meeting of Applied Physics); aldazine derivatives (Japanese Patent Application Laid-Open No. Heisei 2 (1990)-220393); pyrazine derivatives (Japanese Patent Application Laid-Open No. Heisei 2 (1990)-220394); cyclopentadiene derivatives (Japanese Patent Application Laid-Open No. Heisei 2 (1990)-289675); pyrrolopyrrol derivatives (Japanese Patent Application Laid-Open No. Heisei 2 (1990)-296891); styrylamine derivatives (Appl. Phys. Lett., Volume 56, L799 (1990); coumarine compounds (Japanese Patent Application Laid-Open No. Heisei 2 (1990)-191694); and macromolecular compounds described in International Patent Application Publication WO90/13148 and Appl. Phys. Lett., Vol. 158, 18, P1982 (1991).

Further examples of the compounds which are used as the material of the light emitting layer include aromatic dimethylidine compounds disclosed in European Patent No. 0388768 and Japanese Patent Application Laid-Open No. Heisei 3 (1991)-231970. Specific examples of the above compounds include 4,4'-bis(2,2-di-t-butylphenylvinyl) biphenyl (referred to as DTBPBBi, hereinafter), 4,4'-bis(2, 2-diphenylvinyl)biphenyl (referred to as DPVBi, hereinafter) and derivatives of these compounds.

Still further examples of the compounds which are used as the material of the light emitting layer include compounds represented by the general formula (Rs—Q)$_2$—Al—O—L. In the general formula, L represents a hydrocarbon group having 6 to 24 carbon atoms which comprises a phenyl portion, O—L represents a phenolate ligand, Q represents a 8-quilinolate ligand and Rs represents a substituent to the 8-quinolinolate ring which is selected so as to inhibit coordination of more than two 8-quinolinolate ligands to the aluminum atom. Specific examples of the above compound include bis(2-methyl-8-quinolinolato)(para-phenylphenolato)aluminum-(III) and bis (2-methyl-8-quinolinolato)(1-naphtholato)aluminum(III).

Mixed emission of blue light and green light can be obtained in a high efficiency in accordance with the doping method as disclosed in Japanese Patent Application Laid-Open No. Heisei 6 (1994)-9953. In this method, the light emitting material described above can be used as the host. As the dopant, a fluorescent die having strong blue to green color such as a coumarine fluorescent die and the same fluorescent die as that used for the host can be used. Specifically, a light emitting material having a distyrylarylene skeleton structure and preferably DPVBi is used as the host and a diphenylaminovinylarylene and preferably N-diphenylaminovinylbenzene (DPAVB) is used as the dopant.

The light emitting layer for obtaining emission of white light is not particularly limited. The following light emitting layers may be used:

(1) A light emitting layer in which the energy level of each layer in an organic EL laminate is specified and light is emitted utilizing the tunnel injection (European Patent No. 0390551).

(2) A light emitting device emitting white light which is described in an example of a device utilizing the tunnel injection similarly to the device in (1) (Japanese Patent Application Laid-Open No. Heisei 3(1991)-230584).

(3) A light emitting layer having a two-layer structure (Japanese Patent Application Laid-Open Nos. Heisei 2(1990)-220390 and Heisei 2(1990)-216790).

(4) A light emitting layer divided into a plurality of layers each of which is composed of a material having a different wavelength of emitted light (Japanese Patent Application Laid-Open No. Heisei 4(1992)-51491).

(5) A light emitting layer in which a light emitting material emitting blue light (the peak wavelength of the fluorescence: 380 to 480 nm) and a light emitting material emitting green light (the peak wavelength of the fluorescence: 480 to 580 nm) are laminated and a fluorescent material emitting red light is further contained (Japanese Patent Application Laid-Open No. Heisei 6(1994)-207170).

(6) A light emitting layer in which a light emitting layer emitting blue light contains a fluorescent die emitting blue light, a light emitting layer emitting green light has an area containing a fluorescent die emitting red light and a fluorescent material emitting green light is further contained (Japanese Patent Application Laid-Open No. Heisei 7(1995)-142169).

Among these light emitting layers, the light emitting layer having structure (5) is preferably used.

As the fluorescent material emitting red light, compounds shown in the following are preferably used.

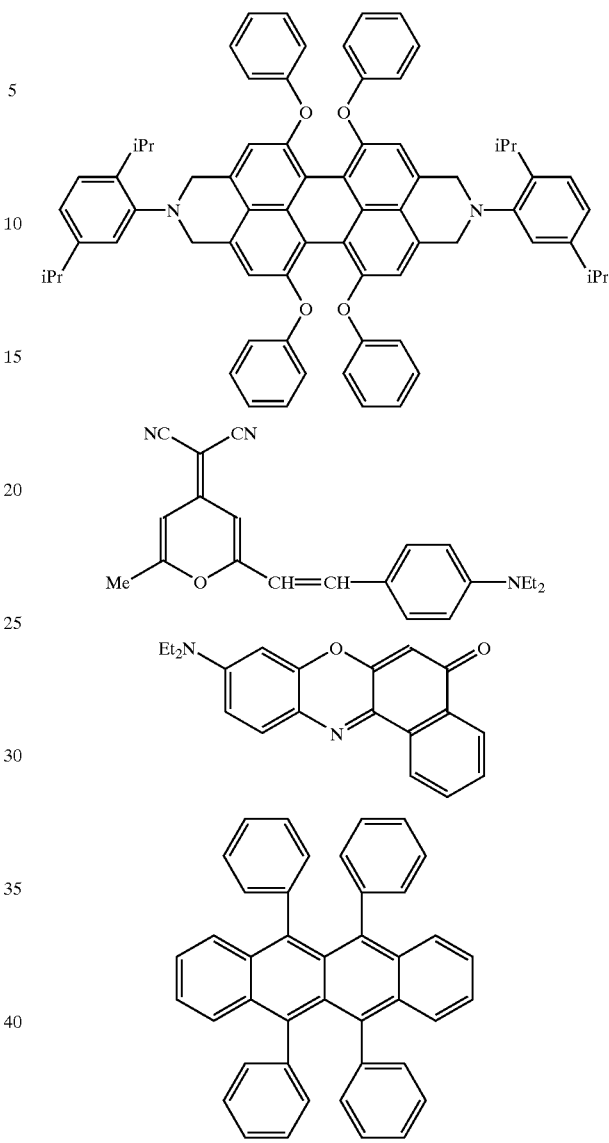

When the amine compound represented by general formula (I) of the present invention is used in the hole transporting area such as the hole transporting layer, any light emitting material can be used. However, the amine compound of the present invention can be used advantageously when a light emitting material emitting blue to green light is used. In particular, the amine compound of the present invention exhibits a remarkable synergistic effect when a compound having a styryl group in the molecule is used as the light emitting material. Specifically, when any of the aromatic compounds having a styryl group which are represented by the following general formulae (III) to (V) is used, the effect of exhibiting a great luminance and achieving a long life can be obtained.

The aromatic compound having a styryl group is, in general, used in the light emitting layer. However, the same effect can be obtained even when the aromatic compound having a styryl group is used in an area other than the light emitting layer such as the hole injecting layer, the hole transporting layer and the electron injecting layer.

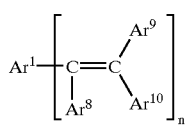

In general formula (III), $Ar^7$ represents an aromatic group having 5 to 40 nuclear atoms which may have substituents, $Ar^8$, $Ar^9$ and $Ar^{10}$ each represent hydrogen atom or an aryl group having 5 to 30 nuclear atoms which may have substituents, at least one of $Ar^8$, $Ar^9$ and $Ar^{10}$ represents an aryl group which may have substituents and n represents an integer of 1 to 6.

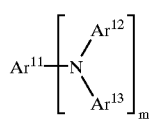

In general formula (IV), $Ar^{11}$ represents an aromatic group having 5 to 30 nuclear atoms which may have substituents, $Ar^{12}$ and $Ar^{13}$ each represent hydrogen atom or an aryl group having 5 to 30 nuclear atoms which may have substituents, at least one of the groups represented by $Ar^{11}$, $Ar^{12}$ and $Ar^{13}$ is substituted with a styryl group which may have substituents and m represents an integer of 1 to 6.

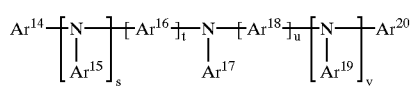

In general formula (V), $Ar^{14}$ and $Ar^{20}$ each represent an aryl group having 5 to 30 nuclear atoms which may have substituents, $Ar^{15}$ to $Ar^{19}$ each represent hydrogen atom or an aromatic group having 5 to 30 nuclear atoms which may have substituents, at least one of the groups represented by $Ar^{15}$ to $Ar^{19}$ is substituted with a styryl group which may have substituents and s, t, u, and v each represents a number of 0 or 1.

Examples of the aryl group having 5 to 30 nuclear atoms in general formulae (III) to (V) include the groups which are described above as the examples of the corresponding groups represented by $Ar^1$ to $Ar^4$ in general formula (I). The aromatic group in general formulae (III) and (IV) is an aromatic group having a valency of 1 to 6 corresponding to the values of n and m, respectively. Examples of the monovalent aromatic group include the groups described above as the examples of the aryl group having 5 to 30 nuclear atoms. Examples of the aromatic groups having a valency of 2 to 6 include groups having a valency of 2 to 6 corresponding to the above aryl groups.

Examples of the substituents which the groups represented by $Ar^7$ to $Ar^{20}$ may have include the groups described as the examples of the groups which the groups represented by $Ar^1$ to $Ar^6$ in general formula (I) may have. When the groups represented by $Ar^7$ to $Ar^{20}$ have two or more substituents, the substituents may be bonded to each other and form a ring.

Typical examples of the compounds represented by general formulae (III) to (V) include 4,4"-bis(2,2-diphenylvinyl-1-yl)-p-terphenylene (referred to as DPVTP, hereinafter), 4,4'-bis(2-(4-(N,N-diphenylamino)phenyl)-vinyl-1-yl)biphenylene (referred to as DPAVBi, hereinafter), 9,10-bis(N-(4-(2,2-diphenyl)vinyl-1-yl)phenyl)-N-phenyl) aminoanthracene (referred to as DPDAA, hereinafter) and N,N'-bis(4-(2,2-diphenyl)vinyl-1-yl)phenyl-N,N'-diphenyl-4,4'-benzidine (referred to as DPTPD, hereinafter).

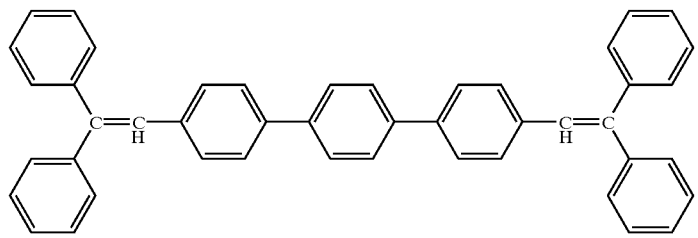

DPVTP

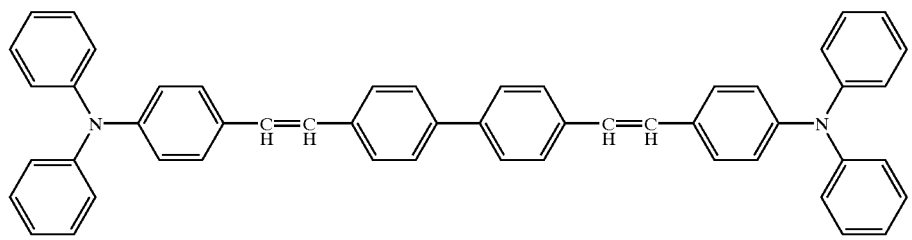

DPAVBi

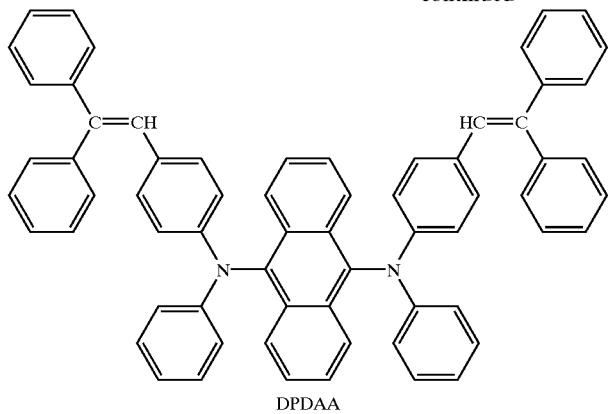

DPDAA

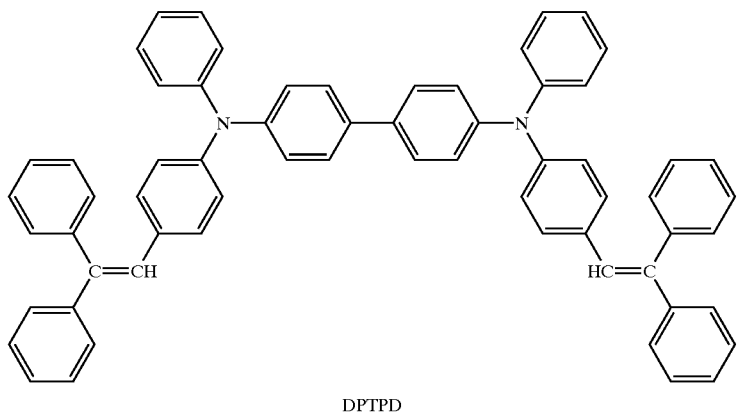

DPTPD

As the process for forming the light emitting layer using the above material, for example, a conventional process such as the vapor deposition process, the spin coating process and the LB process can be used. In particular, it is preferable the light emitting layer is a molecular deposition film. The molecular deposition film is a film formed by deposition of a material compound in the gas phase or a film formed by solidification of a material compound in a solution or in the liquid state. The molecular deposition film can be distinguished from a thin film formed by the LB process (a molecular accumulation film) based on differences in the aggregation structure and the higher order structures and functional differences due to these structural differences.

As disclosed in Japanese Patent Application Laid-Open No. Showa 57(1982)-51781, the light emitting layer can also be formed by dissolving a binding material such as a resin and a material compound into a solvent to prepare a solution, followed by forming a thin film in accordance with the spin coating process.

The thickness of the light emitting layer thus formed is not particularly limited and can be suitably selected in accordance with the situation. It is preferable that the thickness is in the range of 5 nm to 5 μm. The light emitting layer may be constituted with a single layer comprising one or more materials selected from the above materials or may be a laminate of the above light emitting layer with a light emitting layer comprising a compound different from the compound comprised in the above light emitting layer.

The hole injecting and transporting layer is a layer which helps injection of holes into the light emitting layer and transports holes to the light emitting area. This layer has a great mobility of holes and the ionization energy is, in general, as small as 5.5 eV or smaller. For the hole injecting and transporting layer, a material transporting holes to the light emitting layer under a small electric field strength is preferable. It is preferable that the mobility of holes is, for example, at least $10^{-4}$ cm$^2$/V·sec when an electric field of $10^4$ to $10^6$ V/cm is applied.

It is preferable that the amine compound represented by general formula (I) of the present invention is used as the material of the hole injecting and transporting material. The hole injecting and transporting layer may be formed with the compound of the present invention alone or with a mixture of the compound of the present invention with other materials.

The material which is mixed with the amine compound represented by general formula (I) of the present invention and forms the hole injecting and transporting layer is not particularly limited as long as the material has the desirable properties described above. A material can be suitably selected from materials conventionally used as the hole transporting material in optically conductive materials and materials conventionally used for a hole injecting layer in EL devices.

Examples of the material forming the hole injecting and transporting layer are as follows: triazole derivatives (U.S. Pat. No. 3,112,197); oxadiazole derivatives (U.S. Pat. No. 3,189,447); imidazole derivatives (Japanese Patent Application Publication No. Showa 37(1962)-16096); polyarylalkane derivatives (U.S. Pat. Nos. 3,615,402, 3,820,989 and 3,542,544, Japanese Patent Application Publication Nos. Showa 45(1970)-555 and Showa 51(1976)-10983 and Japanese Patent Application Laid-Open Nos. Showa 51(1976)-93224, Showa 55(1980)-17105, Showa 56(1981)-4148, Showa 55(1980)-108667, Showa 55(1980)-156953 and Showa 56(1981)-36656); pyrazoline derivatives and pyrazolone derivatives (U.S. Pat. Nos. 3,180,729 and 4,278,746 and Japanese Patent Application Laid-Open Nos. Showa 55(1980)-88064, Showa 55(1980)-88065, Showa 49(1974)-105537, Showa 55(1980)-51086, Showa 56(1981)-80051, Showa 56(1981)-88141, Showa 57(1982)-45545, Showa 54(1979)-112637 and Showa 55(1980)-74546); phenylenediamine derivatives (U.S. Pat. No. 3,615,404, Japanese Patent Application Publication Nos. Showa 51(1976)-10105, Showa 46(1971)-3712 and Showa 47(1972)-25336 and Japanese Patent Application Laid-Open Nos. Showa 54(1979)-53435, Showa 54(1979)-110536 and Showa 54(1979)-119925); arylamine derivatives (U.S. Pat. Nos. 3,567,450, 3,180,703, 3,240,597, 3,658,520, 4,232,103, 4,175,961 and 4,012,376, Japanese Patent Application Publication Nos. Showa 49(1974)-35702 and Showa 39(1964)-27577, Japanese Patent Application Laid-Open Nos. Showa 55(1980)-144250, Showa 56(1981)-119132 and Showa 56(1981)-22437 and West German Patent No. 1,110,518); chalcone derivatives substituted with amines (U.S. Pat. No. 3,526,501); oxazole derivatives (U.S. Pat. No. 3,257,203); styrylanthracene derivatives (Japanese Patent Application Laid-Open No. Showa 56(1981)-46234); fluorenone derivatives (Japanese Patent Application Laid-Open No. Showa 54(1979)-110837); hydrazone derivatives (U.S. Pat. No. 3,717,462 and Japanese Patent Application Laid-Open Nos. Showa 54(1979)-59143, Showa 55(1980)-52063, Showa 55(1980)-52064, Showa 55(1980)-46760, Showa 55(1980)-85495, Showa 57(1982)-11350, Showa 57(1982)-148749 and Heisei 2(1990)-311591); stilbene derivatives (Japanese Patent Application Laid-Open Nos. Showa 61(1986)-210363, Showa 61(1986)-228451, Showa 61(1986)-14642, Showa 61(1986)-72255, Showa 62(1987)-47646, Showa 62(1987)-36674, Showa 62(1987)-10652, Showa 62(1987)-30255, Showa 60(1985)-93455, Showa 60(1985)-94462, Showa 60(1985)-174749 and Showa 60(1985)- 175052); Silazane derivatives (U.S. Pat. No. 4,950,950); polysilane compounds (Japanese Patent Application Laid-Open No. Heisei 2(1990)-204996); aniline copolymers (Japanese Patent Application Laid-Open No. Heisei 2(1990)-282263); and electrically conductive macromolecular oligomers, in particular, thiophene oligomers (Japanese Patent Application Laid-Open No. Heisei 1(1989)-211399).

As the material of the hole injecting layer, the above materials can be used. The following materials can also be used as the material of the hole injecting layer: porphyrin compounds (Japanese Patent Application Laid-Open No. Showa 63(1988)-295695); and aromatic tertiary-amine compounds and styrylamine compounds (U.S. Pat. No. 4,127,412 and Japanese Patent Application Laid-Open Nos. Showa 53(1978)-27033, Showa 54(1979)-58445, Showa 54(1979)-149634, Showa 54(1979)-64299, Showa 55(1980)-79450, Showa 55(1980)-144250, Showa 56(1981)-119132, Showa 61(1986)-295558, Showa 61(1986)-98353 and Showa 63(1988)-295695). Among the above materials, aromatic tertiary-amine compounds are preferable.

Further examples include compounds having two condensed aromatic rings in the molecule which are disclosed in U.S. Pat. No. 5,061,569, such as 4,4'-bis(N-(1-naphthyl)-N-phenylamino)biphenyl (referred to as NPD, hereinafter) and compounds having three triphenylamine units bonded in the star burst form, which are disclosed in Japanese Patent Application Laid-Open No. Heisei 4(1992)-308688, such as 4,4',4'-tris(N-(3-methylphenyl)-N-phenylamino) triphenylamine (referred to as MTDATA, hereinafter).

Further, aromatic dimethylidine compounds described above as the material of the light emitting layer and inorganic compounds such as the p-type Si and the p-type SiC can also be used as the material of the hole injecting layer.

To form the hole injecting and transporting layer, a thin film of the above compound is formed in accordance with a conventional process such as the vacuum vapor deposition process, the spin coating process, the casting process and the LB process. The thickness of the hole injecting and transporting layer is not particularly limited. The thickness is, in general, 5 nm to 5 μm. As long as the compound of the present invention is contained in the hole transporting area, the hole injecting and transporting layer may be composed of a single layer comprising one or more materials selected from the materials described above or may be a laminate of the above hole injecting and transporting layer with a hole injecting and transporting layer comprising a compounds different from the compound comprised in the above hole injecting and transporting layer.

The layer of an organic semiconductor is a layer for helping injection of holes or electrons into the light emitting layer. It is preferable that this layer has an electric conductivity of $10^{-10}$ S/cm or greater. As the material of the layer of an organic semiconductor, electrically conductive oligomers such as oligomers containing thiophene, oligomers containing arylamines disclosed in Japanese Patent Application Laid-Open No. Heisei 8(1996)-193191 and electrically conductive dendrimers such as dendrimers containing arylamines can be used.

The electron injecting layer is a layer for helping injection of electrons into the light emitting layer and has a great mobility of electrons. The layer for improving adhesion is the electron injecting layer made of a material exhibiting excellent adhesion with the cathode. As the material used for the electron injecting layer, metal complexes of 8-hydroxyquinoline and derivatives thereof are preferably used. Examples of the metal complexes of 8-hydroxyquinoline and derivatives thereof include metal chelate compounds of oxinoid compounds including chelate compounds of oxine (in general, 8-quinolinol or 8-hydroxyquinoline). For example, Alq described in the light emitting material can be used.

Examples of the oxadiazole derivative include electron transferring compounds represented by the following general formulae:

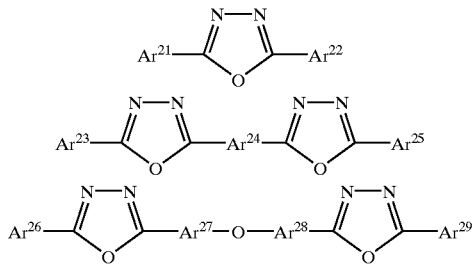

wherein $Ar^{21}$, $Ar^{22}$, $Ar^{23}$, $Ar^{25}$ and $Ar^{26}$ each represent an aryl group which may have substituents, $Ar^{21}$, $Ar^{22}$, $Ar^{23}$, $Ar^{24}$, $Ar^{25}$ and $Ar^{26}$ may represent the same group or different groups, $Ar^{24}$, $Ar^{27}$ and $Ar^{28}$ each represent an arylene group which may have substituents and $Ar^{24}$, $Ar^{27}$ and $Ar^{28}$ may represent the same group or different groups.

Examples of the aryl group in the above general formulae include phenyl group, biphenyl group, anthranyl group, perylenyl group and pyrenyl group. Examples of the arylene group include phenylene group, naphthylene group, biphenylene group, anthranylene group, perylenylene group and pyrenylene group. Examples of the substituent which the above groups may have include alkyl groups having 1 to 10 carbon atoms, alkoxy groups having 1 to 10 carbon atoms and cyano group. As the electron transferring compound, compounds having the excellent property to form a thin layer are used.

Specific examples of the electron transferring compound include the following compounds:

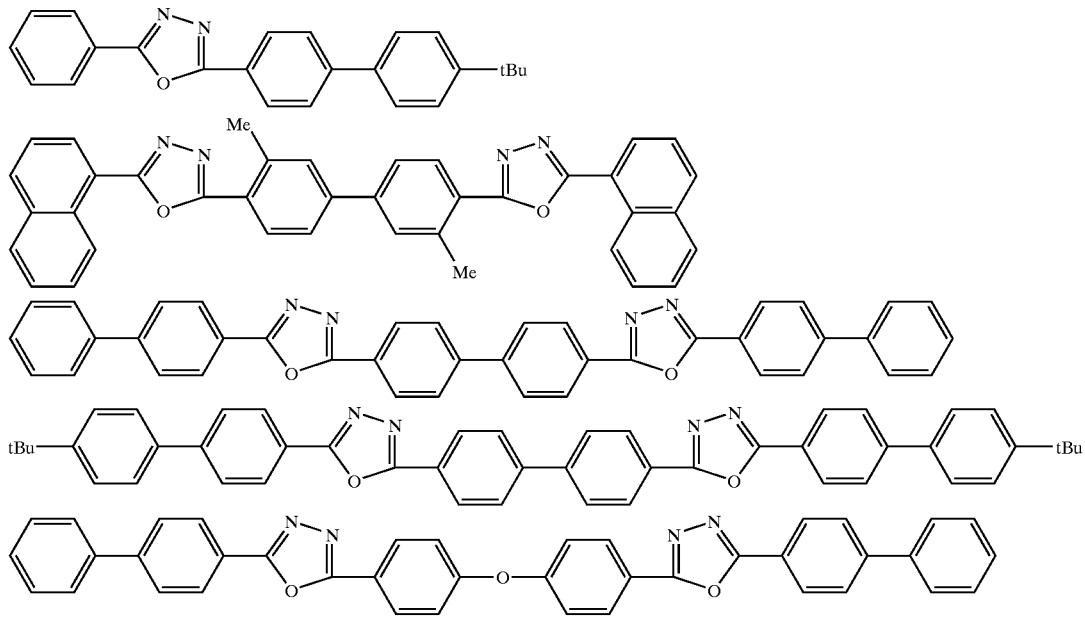

An electron injecting layer comprising an oxide or a halide of an alkali metal or an alkaline earth metal may be disposed. Examples of the oxide or the halide of an alkali metal or an alkaline earth metal include lithium fluoride, lithium oxide, cesium fluoride, cesium oxide, magnesium oxide, magnesium fluoride, calcium oxide and calcium fluoride.

It is also possible that a small amount of an alkali metal, an alkaline earth metal or a compound of these metals is added to a layer of an organic compound and an electron injecting area is formed. It is preferable that the above metal or the compound of the metal is added in an amount of 0.1 to 10% by mole.

As the cathode, a metal, an alloy, an electrically conductive compound or a mixture of these materials which has a small work function (4 eV or smaller) is used as the electrode material. Examples of the electrode material include sodium, sodium-potassium alloys, magnesium, lithium, magnesium-silver alloys, aluminum/aluminum oxide, aluminum-lithium alloys, indium and rare earth metals.

The cathode can be formed by forming a thin film of the above material in accordance with a process such as the vapor deposition process and the sputtering process.

When light emitted from the light emitting layer is obtained through the cathode, it is preferable that the transmittance of the emitted light through the cathode is greater than 10%. It is also preferable that the sheet resistivity of the cathode is several hundred $\Omega/\square$ or smaller. The thickness of the cathode is selected, in general, in the range of 10 nm to 1 $\mu$m and preferably in the range of 50 to 200 nm.

In an organic EL device, since an electric field is applied to an ultra-thin film, defects tend to be formed in pixels of images due to leak and short circuit. It is preferable that an insulating thin layer is inserted between a pair of electrodes to prevent the formation of defects.

Examples of the material used for the insulating layer include aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide and vanadium oxide.

The above materials may be used singly or as a mixture. The above materials may be used as a laminate.

As for the process for preparing the organic EL device of the present invention, the organic EL device can be prepared by forming the anode, the light emitting layer and, where necessary, the hole injecting layer and the electron injecting layer using the above materials in accordance with the above process, followed by forming the cathode. The organic EL device may be prepared in the reverse order, i.e., by preparing the cathode first and the anode last.

As an embodiment, preparation of an organic EL device having the construction in which an anode, a hole injecting layer, a light emitting layer, an electron injecting layer and a cathode are formed on a substrate transmitting light in this order will be described in the following.

The anode is formed first. A thin film of an anode material is formed on the substrate transmitting light in accordance with a process such as the vapor deposition process or the sputtering process so that the formed thin film has a thickness of 1 $\mu$m or smaller and preferably in the range of 10 to 200 nm. The hole injecting layer is then formed on the anode. As described above, the hole injecting layer may be formed in accordance with a process such as the vacuum vapor deposition process, the spin coating process, the casting process and the LB process. The vacuum vapor deposition process is preferable since a uniform film can be obtained and the formation of pin holes can be suppressed. When the hole injecting layer is formed in accordance with the vacuum vapor deposition process, the conditions of the vacuum vapor deposition process are different depending on the compound used (the material of the hole injecting layer) and the crystal structure and the recombination structure of the hole injecting layer to be formed. In general, it is preferable that the temperature of the source of the vapor deposition is selected in the range of 50 to 450° C., the degree of vacuum is selected in the range of $10^{-7}$ to $10^{-3}$ torr, the rate of vapor deposition is selected in the range of 0.01 to 50 nm/second, the temperature of the substrate plate is selected in the range of −50 to 300° C. and the thickness of the film is selected in the range of 5 nm to 5 $\mu$m.

The light emitting layer is formed on the hole injecting layer. Using a desired organic light emitting material, a thin film of the organic light emitting material is formed in accordance with a process such as the vacuum vapor deposition process, the spin coating process, the casting process and the LB process. The vacuum vapor deposition process is preferable since a uniform film can be obtained and the formation of pin holes can be suppressed. When the light emitting layer is formed in accordance with the vacuum vapor deposition process, the conditions of the vacuum vapor deposition process is different depending on the compound used. In general, the conditions can be selected in the same ranges as those described above in the formation of the hole injecting layer.

The electron injecting layer is formed on the light emitting layer formed above. Similarly to the formation of the hole injecting layer and the light emitting layer, it is preferable that the vacuum vapor deposition process is used since the formation of a uniform film is necessary. The conditions of the vacuum vapor deposition process can be selected in the same ranges as those described in the formation of the hole injecting layer and the light emitting layer.

The present invention may be used in various manners in accordance with the type of the layer in the hole transporting area in which the compound is used. When the vacuum deposition process is used, the compound can be vacuum vapor deposited simultaneously with other materials. When the spin coating process is used, the compound can be used as a mixture with other materials.

The cathode is laminated in the final step and the organic EL device can be obtained. The cathode is constituted with a metal and the vacuum vapor deposition process or the sputtering process can be used for the formation. The vacuum vapor deposition process is preferable since formation of damages in the organic layers formed in previous steps during the formation of the cathode can be prevented.

It is preferable that the steps for preparing the organic EL device from the formation of the anode to the formation of the cathode are conducted after the pressure in the apparatus for the preparation is reduced and while the pressure is maintained at the reduced pressure.

When the organic EL device is used, the light emission can be observed when the anode is connected to the positive electrode (+) and the cathode is connected to the negative electrode (−) and a voltage of 5 to 40 V is applied. When the anode is connected to the negative electrode (−) and the cathode is connected to the positive electrode (+), the light emission is not observed at all. When an alternating voltage is applied, a uniform emission of light is observed only when the anode is connected to the positive electrode (+) and the cathode is connected to the negative electrode (−). The wave form of the applied alternating voltage is not limited.

The present invention will be described more specifically with reference to examples in the following. However, the present invention is not limited to the examples.

EXAMPLES 1 TO 6

Preparation of Amine Compounds

Example 1

(1) Preparation of m-terphenylene Iodide

Into a three-necked flask, 500 g of m-terphenyl (manufactured by ALDRICH Company), 100 g of hydroiodic acid dihydrate, 150 g of iodine, 1.5 liters of acetic acid and 50 ml of concentrated sulfuric acid were placed and the reaction was allowed to proceed at 70° C. for 3 hours. After the reaction was completed, the resultant reaction mixture was poured into 10 liters of methanol and the resultant mixture was stirred for 1 hour and then filtered. The obtained crystals were purified in accordance with the column chromatography, recrystallized from acetonitrile and 128 g of 3'-phenyl-4-iodobiphneyl (IMT) and 34 g of 3-phenyl-5-iodobiphenyl (IMT') were obtained.

(2) Preparation of N,N'-(naphthyl-1-yl)-4,4'-benzidine

Into a 2 liter three-necked flask, 100 g of 1-acetamidonaphthalene (manufactured by TOKYO KASEI Co., Ltd.), 100 g of 4,4'-diiodobiphenyl, 80 g of potassium carbonate, 10 g of copper powder and 1,000 ml of nitrobenzene were placed and the resultant mixture was heated to 200° C. and stirred for 64 hours. After the reaction was completed, inorganic substances were removed by filtration and the solvent in the filtrate was removed by distillation. The obtained residue and 1 liter of tetrahydrofuran were placed into a 3 liter three-necked flask. To the obtained mixture, a solution obtained by dissolving 50 g of potassium hydroxide into 300 ml of methanol was added and the resultant mixture was heated under the refluxing condition for 24 hours. After the reaction was completed, the reaction mixture was poured into 10 liters of ethyl acetate and the resultant mixture was stirred for 1 hour and then filtered. The obtained crystals were purified in accordance with the column chromatography and 38 g of N,N'-(naphthyl-1-yl)-4,4'-benzidine (NB) was obtained.

(3) Preparation of Compound (MT-01)

Into a 300 ml three-necked flask, 10 g of N,N'-diphenyl-4,4'-benzidine (manufactured by HIROSHIMA WAKO Co., Ltd.), 25 g of IMT, 10 g of potassium carbonate, 1 g of copper powder and 100 ml of nitrobenzene were placed and the resultant mixture was heated at 200° C. and stirred for 48 hours. After the reaction was completed, inorganic substances were removed by filtration and the solvent in the filtrate was removed by distillation. The obtained residue was purified in accordance with the column chromatography using a column packed with silica gel (manufactured by HIROSHIMA WAKO Co., Ltd.; C-200) and toluene as the developing solvent and 9.8 g of white powder was obtained.

The FD-MS of the product had a major peak of m/z=793 which corresponds to $C_{60}H_{44}N_2$=792. Therefore, the product was identified to be N,N'-bis(3'-phenylbiphenyl-4-yl)-N,N'-diphenyl-4,4'-benzidine (the glass transition temperature: 114° C.).

This compound was soluble in methylene chloride, toluene and tetrahydrofuran.

Example 2

Preparation of Compound (MT-02)

Into a 300 ml three-necked flask, 10 g of N,N'-diacetyl-4,4'-benzidine (manufactured by TOKYO KASEI Co., Ltd.), 50 g of IMT, 10 g of potassium carbonate, 1 g of copper powder and 100 ml of nitrobenzene were placed and the resultant mixture was heated at 200° C. and stirred for 96 hours. After the reaction was completed, inorganic substances were removed by filtration and the solvent in the filtrate was removed by distillation. The obtained residue was purified in accordance with the column chromatography using a column packed with silica gel (manufactured by HIROSHIMA WAKO Co., Ltd.; C-200) and toluene as the developing solvent and 1.4 g of white powder was obtained.

The FD-MS of the product had a major peak of m/z=1097 which corresponds to $C_{84}H_{60}N_2$=1096. Therefore, the product was identified to be N,N,N',N'-tetrakis(3'-phenylbiphenyl-4-yl)-4,4'-benzidine (the glass transition temperature: 167° C.).

This compound was soluble in methylene chloride, toluene and tetrahydrofuran.

Example 3

Preparation of Compound (MT-03)

Into a 300 ml three-necked flask, 10 g of N,N'-diphenyl-4,4'-benzidine (manufactured by HIROSHIMA WAKO Co., Ltd.), 25 g of IMT', 10 g of potassium carbonate, 1 g of copper powder and 100 ml of nitrobenzene were placed and the resultant mixture was heated at 200° C. and stirred for 48 hours.

After the reaction was completed, inorganic substances were removed by filtration and the solvent in the filtrate was removed by distillation. The obtained residue was purified in accordance with the column chromatography using a column packed with silica gel (manufactured by HIROSHIMA WAKO Co., Ltd.; C-200) and toluene as the developing solvent and 7.7 g of white powder was obtained.

The FD-MS of the product had a major peak of m/z=793 which corresponds to $C_{60}H_{44}N_2$=792. Therefore, the product was identified to be N,N'-bis(3,5-diphenyl-1-yl)-N,N'-diphenyl-4,4'-benzidine (the glass transition temperature: 108° C.).

This compound was soluble in methylene chloride, toluene and tetrahydrofuran.

Example 4

Preparation of Compound (MT-04)

Into a 300 ml three-necked flask, 10 g of N,N-diacetyl-4,4'-benzidine (manufactured by TOKYO KASEI Co., Ltd.), 50 g of IMT, 10 g of potassium carbonate, 1 g of copper powder and 100 ml of nitrobenzene were placed and the resultant mixture was heated at 200° C. and stirred for 96 hours.

After the reaction was completed, inorganic substances were removed by filtration and the solvent in the filtrate was removed by distillation. The obtained residue was purified in accordance with the column chromatography using a column packed with silica gel (manufactured by HIROSHIMA WAKO Co., Ltd.; C-200) and toluene as the developing solvent and 0.4 g of white powder was obtained.

The FD-MS of the product had a major peak of m/z=1097 which corresponds to $C_{84}H_{60}N_2$=1096. Therefore, the product was identified to be N,N,N,N'-tetrakis(3,5-diphenyl-1-yl)-4,4'-benzidine (the glass transition temperature: 148° C.).

This compound was soluble in methylene chloride, toluene and tetrahydrofuran.

Example 5

Preparation of (MT-05)

Into a 300 ml three-necked flask, 10 g of NB, 25 g of IMT, 10 g of potassium carbonate, 1 g of copper powder and 100 ml of nitrobenzene were placed and the resultant mixture was heated at 200° C. and stirred for 48 hours.

After the reaction was completed, inorganic substances were removed by filtration and the solvent in the filtrate was removed by distillation. The obtained residue was purified in accordance with the column chromatography using a column packed with silica gel (manufactured by HIROSHIMA WAKO Co., Ltd.; C-200) and toluene as the developing solvent and 9.6 g of light yellow powder was obtained.

The FD-MS of the product had a major peak of m/z=893 which corresponds to $C_{68}H_{48}N_2$=892. Therefore, the product was identified to be N,N'-bis(3'-phenylbiphenyl-4-yl)-N,N'-di(naphthyl-1-yl)-4,4'-benzidine (the glass transition temperature: 146° C.).

This compound was soluble in methylene chloride, toluene and tetrahydrofuran.

Example 6

Preparation of (MT-06)

Into a 300 ml three-necked flask, 10 g of NB (manufactured by HIROSHIMA WAKO Co., Ltd.), 25 g of IMT, 10 g of potassium carbonate, 1 g of copper powder and 100 ml of nitrobenzene were placed and the resultant mixture was heated at 200° C. and stirred for 48 hours.

After the reaction was completed, inorganic substances were removed filtration and the solvent in the filtrate was removed by distillation. The obtained residue was purified in accordance with the column chromatography using a column packed with silica gel (manufactured by HIROSHIMA WAKO Co., Ltd.; C-200) and toluene as the developing solvent and 7.4 g of light yellow powder was obtained.

The FD-MS of the product had a major peak of m/z=893 which corresponds to $C_{68}H_{48}N_2$=892. Therefore, the product was identified to be N,N'-bis(3,5-diphenyl-1-yl)-N,N'-di(naphthyl-1-yl)-4,4'-benzidine (the glass transition temperature: 139° C.).

This compound was soluble in methylene chloride, toluene and tetrahydrofuran.

EXAMPLES 7 TO 12 AND COMPARATIVE EXAMPLES 1 AND 2

Preparation I of Organic EL Devices

Example 7

On a glass substrate of a size of 25 mm×75 mm×1.1 mm, a transparent anode of indium tin oxide having a thickness of 750 angstroms was formed.

This glass substrate was placed in a vacuum vapor deposition apparatus (manufactured by NIPPON SHINKU GIJUTU Co., Ltd.) and the pressure inside the apparatus was reduced to about $10^{-6}$ torr. Then, copper phthalocyanine was vapor deposited on the glass substrate at a rate of 2 angstroms/second and a film having a thickness of 300 angstroms was formed.

On the formed film, compound (MT-01) was vapor deposited and a hole injecting layer having a thickness of 200 angstroms was formed. The rate of vapor deposition was 2 angstroms/second. Then, tris(8-quinolinol) aluminum (Alq) was vapor deposited at a rate of vapor deposition of 50 angstroms/second and a light emitting layer having a thickness of 600 angstroms was formed.

Finally, aluminum and lithium were vapor deposited simultaneously and a cathode having a thickness of 2,000 angstroms was formed. The rate of vapor deposition of aluminum was 10 angstroms/second and the rate of vapor deposition of lithium was 0.1 angstrom/second.

When a voltage of 5 V was applied to the obtained organic EL device, 104 nit of green light was emitted.

After the organic EL device was kept in a thermostat at 100° C. for 100 hours, the efficiency of light emission of the organic EL device was the same as the initial value.

Example 8

An organic EL device was prepared in accordance with the same procedures as those conducted in Example 7 except that MT-02 was used in place of MT-01.

When a voltage of 5 V was applied to the obtained organic EL device, 108 nit of green light was emitted.

After the organic EL device was kept in a thermostat at 100° C. for 100 hours, the efficiency of light emission of the organic EL device was the same as the initial value.

Example 9

An organic EL device was prepared in accordance with the same procedures as those conducted in Example 7 except that MT-03 was used in place of MT-01.

When a voltage of 5 V was applied to the obtained organic EL device, 111 nit of green light was emitted.

After the organic EL device was kept in a thermostat at 100° C. for 100 hours, the efficiency of light emission of the organic EL device was the same as the initial value.

Example 10

An organic EL device was prepared in accordance with the same procedures as those conducted in Example 7 except that MT-04 was used in place of MT-01.

When a voltage of 5 V was applied to the obtained organic EL device, 107 nit of green light was emitted.

After the organic EL device was kept in a thermostat at 100° C. for 100 hours, the efficiency of light emission of the organic EL device was the same as the initial value.

Example 11

An organic EL device was prepared in accordance with the same procedures as those conducted in Example 7 except that MT-05 was used in place of MT-01.

When a voltage of 5 V was applied to the obtained organic EL device, 97 nit of green light was emitted.

After the organic EL device was kept in a thermostat at 100° C. for 100 hours, the efficiency of light emission of the organic EL device was the same as the initial value.

Example 12

An organic EL device was prepared in accordance with the same procedures as those conducted in Example 7 except that MT-06 was used in place of MT-01.

When a voltage of 5 V was applied to the obtained organic EL device, 98 nit of green light was emitted.

After the organic EL device was kept in a thermostat at 100° C. for 100 hours, the efficiency of light emission of the organic EL device was the same as the initial value.

Comparative Example 1

An organic EL device was prepared in accordance with the same procedures as those conducted in Example 7 except that NPD having the following structure was used in place of MT-01.

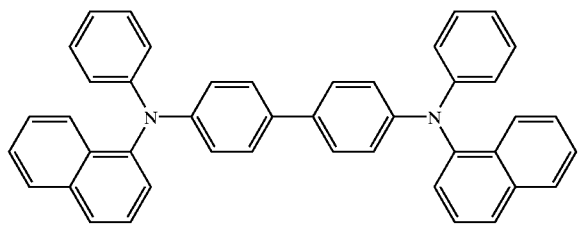

When a voltage of 5 V was applied to the obtained organic EL device, 103 nit of green light was emitted.

After the organic EL device was kept in a thermostat at 100° C. for 100 hours, the efficiency of light emission of the organic EL decreased to a half (50%) of the initial value.

Comparative Example 2

An organic EL device was prepared in accordance with the same procedures as those conducted in Example 7 except that TBA having the following structure was used in place of MT-01.

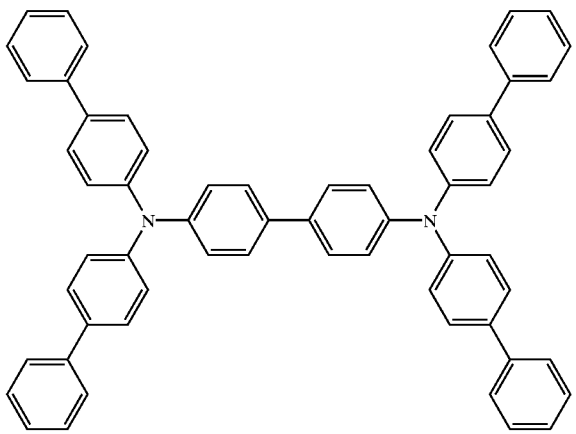

When a voltage of 5 V was applied to the obtained organic EL device, 72 nit of green light was emitted.

Since TBA is insoluble in solvents such as methylene chloride, toluene and tetrahydrofuran, TBA was purified by sublimation. However, impurities could not be removed completely and the luminance of light emission was somewhat smaller.

After the organic EL device was kept in a thermostat at 100° C. for 100 hours, the efficiency of light emission of the organic EL device was the same as the initial value.

The properties of the organic EL devices in Examples 7 to 12 and Comparative Examples 1 and 2 are shown together in Table 1.

TABLE 1

| | Voltage (V) | Luminance (nit) | Color of emitted light | Heat resistance (relative value) (%) |
|---|---|---|---|---|
| Example 7 | 5.0 | 104 | green | 100 |
| Example 8 | 5.0 | 108 | green | 100 |
| Example 9 | 5.0 | 111 | green | 100 |
| Example 10 | 5.0 | 107 | green | 100 |
| Example 11 | 5.0 | 97 | green | 100 |
| Example 12 | 5.0 | 98 | green | 100 |
| Comparative Example 1 | 5.0 | 103 | green | 50 |
| Comparative Example 2 | 5.0 | 72 | green | 100 |

Note: The heat resistance was evaluated by the ratio of the efficiency of light emission after an organic EL device was kept in a thermostat at 100° C. for 100 hours to the initial efficiency of light emission and expressed as the relative value (%).

As shown by comparison of the results in Examples 7 to 12 and the results in Comparative Examples 1 and 2, more excellent luminances of light emission and longer lives under heating (the property of showing no deterioration in the performance under the environment of 100° C.) could be obtained when the amine compound of the present invention was used in the hole transporting area.

EXAMPLES 13 TO 15 AND COMPARATIVE EXAMPLES 3 TO 5

Preparation II of Organic EL Devices

Example 13

An organic EL device was prepared in accordance with the same procedures as those conducted in Example 7 except that DPVTP and DPAVBi were vapor deposited simultaneously to form a film having a thickness of 400 angstroms and then Alq was vapor deposited to form a film having a thickness of 200 angstroms in place of vapor depositing Alq to form a film having a thickness of 600 angstroms.

The rates of vapor deposition of DPVTP and DPAVBi were 10 angstroms/second and 0.2 angstroms/second, respectively.

When a voltage of 5 V was applied to the obtained organic EL device, 112 nit of blue light was emitted.

When this device was driven at the room temperature, the time passed before the luminance decreased to a half of the initial luminance of 500 nit was 2,600 hours.

Example 14

An organic EL device was prepared in accordance with the same procedures as those conducted in Example 13 except that DPDAA was vapor deposited in place of DPVTP.

When a voltage of 6 V was applied to the obtained organic EL device, 83 nit of green light was emitted.

When this device was driven at the room temperature, the time passed before the luminance decreased to a half of the initial luminance of 500 nit was 820 hours.

Example 15

An organic EL device was prepared in accordance with the same procedures as those conducted in Example 13 except that DPTPD was vapor deposited in place of DPVTP.

When a voltage of 6 V was applied to the obtained organic EL device, 101 nit of blue light was emitted.

When this device was driven at the room temperature, the time passed before the luminance decreased to a half of the initial luminance of 500 nit was 720 hours.

Comparative Example 3

An organic EL device was prepared in accordance with the same procedures as those conducted in Example 13 except that TBA was used in place of MT-01.

When a voltage of 6 V was applied to the obtained organic EL device, 87 nit of blue light was emitted.

Since TBA is insoluble in solvents such as methylene chloride, toluene and tetrahydrofuran, TBA was purified by sublimation. However, impurities could not be removed completely and the luminance of light emission was somewhat smaller.

When this device was driven at the room temperature, the time passed before the luminance decreased to a half of the initial luminance of 500 nit was 1,100 hours.

Comparative Example 4

An organic EL device was prepared in accordance with the same procedures as those conducted in Example 14 except that TBA was used in place of MT-01.

When a voltage of 6 V was applied to the obtained organic EL device, 69 nit of green light was emitted.

Since TBA is insoluble in solvents such as methylene chloride, toluene and tetrahydrofuran, TBA was purified by sublimation. However, impurities could not be removed completely and the luminance of light emission was somewhat smaller.

When this device was driven at the room temperature, the time passed before the luminance decreased to a half of the initial luminance of 500 nit was 440 hours.

Comparative Example 5

An organic EL device was prepared in accordance with the same procedures as those conducted in Example 15 except that TBA was used in place of MT-01.

When a voltage of 6 V was applied to the obtained organic EL device, 85 nit of blue light was emitted.

Since TBA is insoluble in solvents such as methylene chloride, toluene and tetrahydrofuran, TBA was purified by sublimation. However, impurities could not be removed completely and the luminance of light emission was somewhat smaller.

When this device was driven at the room temperature, the time passed before the luminance decreased to a half of the initial luminance of 500 nit was 340 hours.

The properties of the organic EL devices in Examples 13 to 15 and Comparative Examples 3 to 5 are shown together in Table 2.

TABLE 2

|  | Voltage (V) | Luminance (nit) | Color of emitted light | Half life of luminance (hr) |
| --- | --- | --- | --- | --- |
| Example 13 | 6.0 | 112 | blue | 2600 |
| Example 14 | 6.0 | 83 | green | 820 |
| Example 15 | 6.0 | 101 | blue | 770 |
| Comparative Example 3 | 6.0 | 87 | blue | 1100 |
| Comparative Example 4 | 6.0 | 69 | green | 440 |
| Comparative Example 5 | 6.0 | 85 | blue | 340 |

Note: The half-life of luminance was obtained by driving an organic EL device under a constant current driving at an initial luminance of 500 nit and measuring the time passed before the luminance decreased to 250 nit.

As shown by comparison of the results in Examples 13, 14 and 15 to the results in Comparative Examples 3, 4 and 5, respectively, more excellent luminances and longer lives of luminance could be achieved when the compounds having a styryl group was used in the light emitting layer and the amine compound of the present invention was used in the hole transporting area.

INDUSTRIAL APPLICABILITY

The amine compound represented by general formula (I) of the present invention has a great solubility in organic solvents and can be purified easily.

The amine compound is useful as a component material of an organic EL device and excellent heat resistance is exhibited, in particular, when the amine compound is used in the hole transporting area.

The amine compound represented by general formula (I) of the present invention exhibits the effect of improving the luminance of light emission and the life of luminance when the amine compound is used in the light emitting area and, in particular, when the amine compound is used as a component material of an organic EL device in which a compound having a styryl group is used in the light emitting layer.

What is claimed is:

1. An amine compound represented by the following general formula (I):

$$\mathrm{Ar^1} \diagdown_{\mathrm{N}} - (\mathrm{Ar^5})_p - (\mathrm{X})_r - (\mathrm{Ar^6})_q - \mathrm{N} \diagup^{\mathrm{Ar^3}}_{\mathrm{Ar^4}} \quad (\mathrm{I})$$

where $Ar^1$, $Ar^2$, $Ar^3$ and $Ar^4$ each represents a substituted or unsubstituted aryl group having 5 to 30 nuclear atoms;

at least one of $Ar^1$, $Ar^2$, $Ar^3$ and $Ar^4$ represents a m-terphenyl group;

$Ar^5$ and $Ar^6$ each represents a substituted or unsubstituted arylene group having 5 to 30 nuclear atoms;

X represents O, S, an alkylene group having 1 to 6 carbon atoms, an arylene group having 5 to 30 nuclear atoms or a diphenylmethylene group;

p and q each represents an integer of 0 to 3;

r represents a number of 0 or 1; and p+q>1.

2. The amine compound according to claim 1, wherein at least one of $Ar^1$, $Ar^2$, $Ar^3$ and $Ar^4$ represents a m-terphenyl group and the rest of $Ar^1$, $Ar^2$, $Ar^3$ and $Ar^4$ each represents a phenyl group or a naphthyl group.

3. An organic electroluminescence device comprising at least an organic light emitting layer disposed between a pair of electrodes, wherein the device comprises an amine compound described in claim 2 in a hole transporting layer.

4. The amine compound according to claim 1, wherein the m-terphenyl group is a substituted or unsubstituted group expressed by the following formula (II):

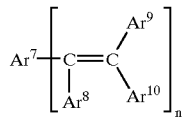

(II)

5. An organic electroluminescence device comprising at least an organic light emitting layer disposed between a pair of electrodes, wherein the device comprises the amine compound described in claim 1.

6. The organic electroluminescence device according to claim 5, wherein the device comprises in the organic light emitting area a compound selected from aromatic compounds having a styryl group which are represented by the following general formulae (III) to (V):

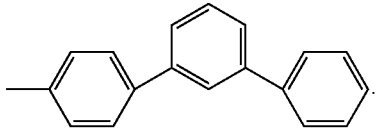

(III)

where $Ar^7$ represents a substituted or unsubstituted aromatic group having 5 to 40 nuclear atoms; $Ar^8$, $Ar^9$ and $Ar^{10}$ each represents a hydrogen atom or a substituted or unsubstituted aryl group having 5 to 30 nuclear atoms; at least one of $Ar^8$, $Ar^9$ and $Ar^{10}$ represents a substituted or unsubstituted aryl group; and n represents an integer of 1 to 6,

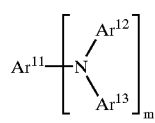

(IV)

where $Ar^{11}$ represents a substituted or unsubstituted aromatic group having 5 to 30 nuclear atoms; $Ar^{12}$ and $Ar^{13}$ each represents a hydrogen atom or a substituted or unsubstituted aryl group having 5 to 30 nuclear atoms; and at least one of the groups represented by $Ar^{11}$, $Ar^{12}$ and $Ar^{13}$ is substituted with a substituted or unsubstituted styryl group; and m represents an integer of 1 to 6, and

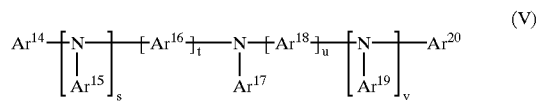

(V)

where $Ar^{14}$ and $Ar^{20}$ each represents a substituted or unsubstituted aryl group having 5 to 30 nuclear atoms; $Ar^{15}$ to $Ar^{19}$ each represents a hydrogen atom or a substituted or unsubstituted aromatic group having 5 to 30 nuclear atoms; at least one of the groups represented by $Ar^{15}$ to $Ar^{19}$ is substituted with a substituted or unsubstituted styryl group; and s, t, u, and v each represents a number of 0 or 1.

7. An organic electroluminescence device comprising at least an organic light emitting layer disposed between a pair of electrodes, wherein the device comprises the amine compound described in claim 1 in a hole transporting area.

8. An amine compound represented by the following general formula (I):

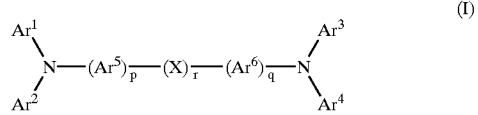

(I)

where $Ar^1$, $Ar^2$, $Ar^3$ and $Ar^4$ each represents a substituted or unsubstituted aryl group having 5 to 30 nuclear atoms;

at least one of $Ar^1$, $Ar^2$, $Ar^3$ and $Ar^4$ represents a substituted m-terphenyl group;

$Ar^5$ and $Ar^6$ each represents a substituted or unsubstituted arylene group having 5 to 30 nuclear atoms;

X represents O, S, an alkylene group having 1 to 6 carbon atoms, an arylene group having 5 to 30 nuclear atoms or a diphenylmethylene group;

p and q each represents an integer of 0 to 3;

r represents a number of 0 or 1;

p+q>1; and the m-terphenyl group is substituted with an alkyl group having 1 to 6 carbon atoms, a styryl group having 8 to 30 carbon atoms, an alkoxy group having 1 to 6 carbon atoms, an aryloxyl group having 5 to 18 carbon atoms, a nitro group, a cyano group, an ester group having 1 to 6 carbon atoms, or a halogen atom.

9. An organic electroluminescence device comprising at least an organic light emitting layer disposed between a pair of electrodes, wherein the device comprises the amine compound described in claim 8.

10. An organic electroluminescence device comprising at least an organic light emitting layer disposed between a pair of electrodes, wherein the device comprises the amine compound described in claim 8 in a hole transporting area.

11. An amine compound represented by the following general formula (I):

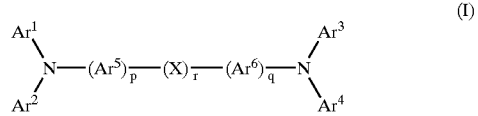

(I)

where $Ar^1$, $Ar^2$, $Ar^3$ and $Ar^4$ each represents a substituted or unsubstituted aryl group having 5 to 30 nuclear atoms;

at least one of $Ar^1$, $Ar^2$, $Ar^3$ and $Ar^4$ represents an unsubstituted m-terphenyl group;

$Ar^5$ and $Ar^6$ each represents a substituted or unsubstituted arylene group having 5 to 30 nuclear atoms;

X represents O, S, an alkylene group having 1 to 6 carbon atoms, an arylene group having 5 to 30 nuclear atoms or a diphenylmethylene group;

p and q each represents an integer of 0 to 3;

r represents a number of 0 or 1; and p+q>1.

12. An organic electroluminescence device comprising at least an organic light emitting layer disposed between a pair of electrodes, wherein the device comprises the amine compound described in claim 11.

13. An organic electroluminescence device comprising at least an organic light emitting layer disposed between a pair of electrodes, wherein the device comprises the amine compound described in claim 11 in a hole transporting area.

* * * * *